United States Patent [19]

Peters

[11] Plant 4,673

[45] Mar. 17, 1981

[54] APRICOT TREE

[76] Inventor: Richard Peters, P.O. Box 907, Fresno, Calif. 93714

[21] Appl. No.: 82,160

[22] Filed: Oct. 5, 1979

[51] Int. Cl.[3] ..... A01H 5/03
[52] U.S. Cl. ..... Plt./39
[58] Field of Search ..... Plt./39

*Primary Examiner*—Robert E. Bagwill
*Attorney, Agent, or Firm*—Huebner & Worrel

[57] ABSTRACT

An apricot tree which bears freestone fruit which most nearly resembles that of the Lulu Belle (unpatented) and Early Perfection (unpatented) but which ripens approximately with the Pomo (U.S. Plant Pat. No. 2,192) which is normally ten days before the Royal (unpatented) or two weeks before the Tilton (unpatented) and which is characterized as to novelty by its uniformly large size for such early maturity, uniformly truncated shape with unequal sides, and the ability to maintain good condition over a protracted harvest season.

1 Drawing Figure

BACKGROUND OF THE VARIETY

The present invention relates to a new and distinct variety of apricot tree broadly characterized by its bearing of fruit which is of good eating quality and relatively early ripening and more particularly characterized by the fruit being of uniformly large size, uniform shape, and having good keeping quality.

The commercial value of a fruit tree is dependent on a number of factors, the lack of any one of which can greatly affect the price brought by the fruit. The well known Tilton and Royal (unpatented) varieties of apricot trees bear symmetrical fruit of medium to large size and good quality. However, the apricots borne by these varieties ripen later then those borne by other varieties such as the Pomo apricot tree (U.S. Plant Pat. No. 2,192) and frequently encounter depressed prices. Generally, the fruit borne by the early varieties is of only medium keeping quality, of inconsistent size and otherwise inferior. It has long been recognized that it would be highly advantageous to provide an apricot tree bearing fruit which ripens relatively early while having good keeping quality and uniformly large size. It is, of course, desirable that the apricots borne by such an improved variety also possess other characteristics desirable in creating consumer acceptance such as uniformity of shape and good eating quality.

ORIGIN AND ASEXUAL REPRODUCTION OF THE NEW VARIETY

The new variety of apricot tree was originated by me in an orchard leased to me and located on the north side of Kings Canyon Road between Clovis and Fowler Avenues near the City of Fresno, in the County of Fresno, in the State of California.

Starting with the Lulu Belle (unpatented) and crossing the progeny with the Royal and Tilton (unpatented) varieties, I produced three generations of unnamed seedlings. I permitted each generation to fruit amd selected the seedlings that produced the best fruit to cross to produce the next generation. The selected trees from the third generation produced early ripening apricots of good size but poor flavor. The selected third generation trees were then crossed with the Royal (unpatented) and the present variety was found in the resultant progeny.

I subsequently asexually reproduced by budding the subject variety of apricot tree in said orchard and in another orchard located near the intersection of Nebraska and Cedar Avenues west of the City of Selma in said County and State. The fruit and tree characteristics of the asexually reproduced trees proved identical to those of the selected seedling.

SUMMARY OF THE NEW VARIETY

The instant variety of apricot tree is characterized by having a trunk which is of medium smooth texture and by having branches which are of a color which is relatively more brown and less red than is normal for apricot trees. The tree bears fruit which ripens approximately ten days earlier than fruit of the Royal and two weeks earlier than the Tilton. The fruit is of a large size, similar to that of the Pomo apricot tree (U.S. Plant Pat. No. 2,192) but is more uniform in size. The fruit borne by the new variety of apricot tree most nearly resembles the fruit of the Lulu Belle or Early perfection. It is uniform in shape, the shape being oblate with unequal sides and including a depressed pistil point. The fruit borne by the instant variety of apricot tree is of excellent eating quality and is noteworthy for its good keeping quality both on the tree and after harvest.

BRIEF DESCRIPTION OF THE DRAWING

The accompanying drawing is a color photograph of mature fruit of the subject variety together with three stones detached therefrom, with two of the fruit divided along the suture plane to show the flesh color.

DETAILED DESCRIPTION

Referring more specifically to the pomological details of this new and distinct variety of apricot tree, the following has been observed under the ecological conditions prevailing in the above designated orchards near Fresno, Calif. All major color code plate identifications are by reference to the A. Maerz and M. Paul Dictionary of Color published by the McGraw-Hill Book Company, Second Edition, 1950.

TREE

Size: Large.
Figure: Spreading.
Productivity: Productive.
Regularity of bearing: Regular.

Trunk:
*Diameter in relation to length.*—Medium.
*Surface characteristics.*—Medium smooth.
Branches:
*Size.*—Medium.
*Surface character.*—Medium smooth.
*Color.*—Laurel Oak, page 37, plate 7, J-10. This color is relatively more brown and less red than the usual color of apricot tree branches.
*Lenticels.*—Number—numerous. Size—1×6 mm to 2×7 mm.
Leaves:
*Size.*—Large.
*Length.*—90 mm.
*Width.*—72 mm.
*Shape.*—Ovate, cordate without sinus.
*Color.*—Upper—Privet, page 71, plate 24, L-6. Lower—Cypress Green, page 69, plate 23, J-7.
*Marginal form.*—Double serrate.
*Glandular characteristics.*—Many, globose.
*Petiole.*—Length—20–25 mm. Thickness—1–2 mm.
*Stem glands.*—Number—1–3. Arrangement—Variable. Size—0.1–0.2 mm. Type—Globose. Color—Maracaibo, page 39, plate 8, L-9.
Flower buds:
*Size.*—Medium to large.
*Shape.*—Obtuse to conical.
*Surface.*—Lightly pubescent.
Flowers:
*Date of bloom.*—First bloom noted Feb. 15, 1977; 90% open on Feb. 26, 1977; petal fall—Mar. 2, 1977.
*Size.*—Medium, 24 mm in diameter.
*Color.*—Upperside—page 25, plate 1, A-7. Lowerside—page 25, plate 1, A-7.
*Number of pistils.*—1.
*Number of stamens.*—25 to 29.

FRUIT

Maturity: June 4–7. Ten days before the Royal and two weeks before the Tilton.
Size: Uniformly large.
*Diameter.*—47–50 mm.
*Transverse in suture plane.*—54–56 mm.
*Transverse at right angles to suture plane.*—50–55 mm.
Form: Shape among fruits uniform.
*Symmetry.*—Oblate, truncate with unequal sides.
*Suture.*—Distinct, slightly depressed, 80–90 mm in length.
*Ventril surface.*—Smooth.
*Stem cavity.*—Acute angle, shallow in depth. 15 mm×8 mm×8 mm deep.
*Base.*—Flat, smoothly rounded on dorsal side, abruptly rounded on suture side.
*Apex.*—Flat and slightly depressed.
*Pistil point.*—Depressed.
*Stem.*—Length—5 mm. Caliper—4 mm.
*Skin.*—Thickness—medium. Texture—medium. Tendency to crack—none. Color—Moresco, page 41, plate 9, J-10. Pubescence—lightly pubescent.
Flesh:
*Color.*—Moresco, page 41, plate 9, J-10.
*Surface of pit cavity.*—Smooth.
*Color of pit well.*—Moresco, page 41, plate 9, K-10.
*Juice.*—Slightly juicy.
*Flavor.*—Sweet, sub-acid, mild flavored.
*Aroma.*—Mildly aromatic, pleasing.
*Texture.*—Fine grained, tender, meaty.
*Ripening.*—Uneven, apex first.
*Eating quality.*—Good.
Stone: Freestone.
*Size.*—Medium. Diameter—13 mm. Transverse in suture plane—20 mm. Transverse at right angles to suture plane—25 mm.
*Form.*—Ovate, slightly flattened at base and a slight point at the apex.
*Sides.*—Very slightly pitted.
*Dorsal suture.*—Wide, raised and decidedly winged.
*Color.*—Raffia, page 45, plate 11, E-5.
Use: Fresh or processed.
Keeping quality: Good.
Shipping quality: Good.

Although the new variety of apricot tree possesses the described characteristics as a result of the growing conditions in Fresno County, Calif., in the Central part of the San Joaquin Valley, it is to be understood that variations of the usual magnitude in characteristics incident to growing conditions, fertilization, pruning and pest control are to be expected.

Having thus described and illustrated my new variety of apricot tree, what is claimed as new and desired to be secured by Letters Patent is:

1. A new and distinct variety of apricot tree substantially as illustrated and described which is characterized by branches which are relatively more brown and less red in color than the branches of other apricot trees, which bears fruit of uniformly truncated shape having uneven sides, which is of large size, which is early ripening, approximately with the Pomo, is of good eating quality resembling the Lulu Belle and Early Perfection; and is particularly characterized by the good holding quality of the fruit before harvest as well as during packing, shipping and display for sale.

* * * * *

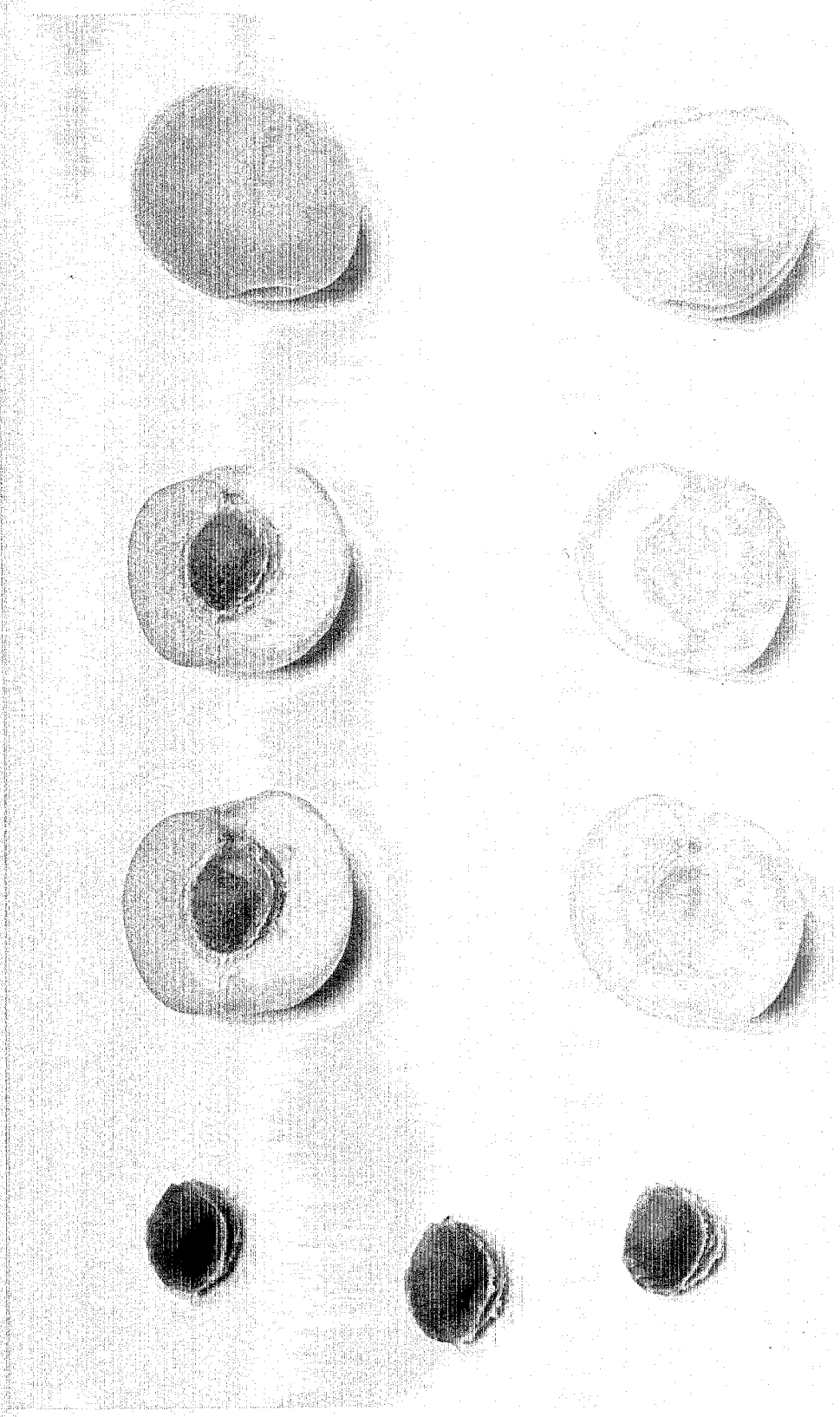

UNITED STATES PATENT AND TRADEMARK OFFICE

CERTIFICATE OF CORRECTION

PATENT NO. : PP 4,673

DATED : March 17, 1981

INVENTOR(S) : Richard Peters

It is certified that error appears in the above-identified patent and that said Letters Patent are hereby corrected as shown below:

Column 1, line 38, delete "amd" and substitute ---and---.

Column 2, line 19, delete "perfection" and substitute ---Perfection---.

Signed and Sealed this

*Seventh* Day of *July 1981*

[SEAL]

*Attest:*

RENE D. TEGTMEYER

*Attesting Officer*

*Acting Commissioner of Patents and Trademarks*